US006617318B1

(12) United States Patent
Nelson et al.

(10) Patent No.: US 6,617,318 B1
(45) Date of Patent: Sep. 9, 2003

(54) METHODS OF PREPARING SUBSTITUTED TETRACYCLINES WITH TRANSITION METAL-BASED CHEMISTRIES

(75) Inventors: Mark L. Nelson, Wellesley, MA (US); Glen Rennie, Weymouth, MA (US); Darrell J. Koza, Westerly, RI (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 09/660,598

(22) Filed: Sep. 13, 2000

Related U.S. Application Data
(60) Provisional application No. 60/232,091, filed on Sep. 12, 2000, and provisional application No. 60/154,701, filed on Sep. 14, 1999.

(51) Int. Cl.[7] .................. A61K 31/65; C07C 233/64
(52) U.S. Cl. ..................................... 514/152; 552/203
(58) Field of Search ........................ 552/203; 514/152

(56) References Cited

U.S. PATENT DOCUMENTS

| | | | |
|---|---|---|---|
| 2,980,584 A | 4/1961 | Hammer | |
| 2,990,331 A | 6/1961 | Neumann et al. | |
| 3,062,717 A | 11/1962 | Hammer | |
| 3,165,531 A | 1/1965 | Blackwood et al. | |
| 3,454,697 A | 7/1969 | Joyner et al. ................ 424/227 |
| 3,557,280 A | 1/1971 | Weber et al. .................. 424/80 |
| 3,674,859 A | 7/1972 | Beutel et al. .................. 424/80 |
| 3,901,942 A | * 8/1975 | Bernardi et al. ............ 560/559 |
| 3,957,980 A | 5/1976 | Noseworthy ................ 424/227 |
| 4,018,889 A | 4/1977 | Armstrong .................... 424/80 |
| 4,024,272 A | 5/1977 | Rogalski et al. ............ 424/275 |
| 4,126,680 A | 11/1978 | Armstrong .................... 424/80 |

OTHER PUBLICATIONS

Csaky, "Cutting's Handbook of Pharmacology", 6th edition, pp. 27–31, 1979.*

Kalanin, "Carbon–carbon bond formation in heterocycles using Ni–and PD–catalyzed reactions," *J. Synthetic Org. Chem.*, 1992, 413.

Negeishi, "Palladium– or Nickel– catalyzed cross coupling. A new selective method for carbon–carbon bond formation," *Acct. Chem. Res.* 1982 15:340.

Sawamuru, "Catalytic asymmetric synthesis by means of secondary interaction between chiral ligands and substrates," *Chem. Rev. 1992, 92:857.*

Ahmad, N. et al., "Polynuclear complexes of bivalent metal ions with antibiotic tetracycline," *J. Chem. Soc. Pak.* 12(2):168–173 (1990).

Koza, D.J., "Synthesis of 7–substituted tetracycline derivatives," *Organic Lett.*, 2(6):815–817 (2000).

Koza, D.J. "The synthesis of 8–substituted tetracycline derivatives, the first 8–position carbon–carbon bond," *Tetrahedron Lett.*, 41:5017–20 (2000).

* cited by examiner

*Primary Examiner*—Barbara P. Badio
(74) *Attorney, Agent, or Firm*—Lahive & Cockfield, LLP; Elizabeth A. Hanley, Esq.; Cynthia M. Soroos

(57) ABSTRACT

The present invention relates to 7-phenyl substituted tetracycline derivatives and compositions thereof.

25 Claims, No Drawings

METHODS OF PREPARING SUBSTITUTED TETRACYCLINES WITH TRANSITION METAL-BASED CHEMISTRIES

RELATED APPLICATIONS

This application claims the benefit of priority under 35 U.S.C. 119(e) to U.S. Provisional Application No. 60/154,701, filed on Sep. 14, 1999, and U.S. Provisional Application No. 60/232,091, filed Sep. 12, 2000, the entire contents of both of which are incorporated herein by reference.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later oxytetracycline became available. The detailed elucidation of the chemical structure of these agents confirmed their similarity and furnished the analytical basis for the production of a third member of this group in 1952, tetracycline. By 1957, a new family of tetracycline compositions characterized chemically by the absence of the position 6 ring-attached OH group present in the earlier compositions was prepared and became publicly available in 1967; and minocycline was in use by 1972. Individual tetracycline-type agents are structurally compared within Table I below, with reference made the following structural formula:

TABLE I

[Structural formula of tetracycline showing positions 1-12 with $H_3C$, OH, H, $N(CH_3)_2$, OH, $CONH_2$, and OH substituents]

| Congener | Substituent(s) | At Carbon Position Nos. |
|---|---|---|
| Chlortetracycline | —Cl | (7) |
| Oxytetracycline | —OH, —H | (5) |
| Demeclocycline | —OH, —H; —Cl | (6; 7) |
| Methacycline | —OH, —H; =$CH_2$ | (5; 6) |
| Doxycycline | —OH, —H; —$CH_3$, —H | (5; 6) |
| Minocycline | —H, —H; —$N(CH_3)_2$ | (6; 7) |

More recent research efforts have focused on developing new tetracycline antibiotic compositions effective under varying therapeutic conditions and routes of administration; and for developing new tetracycline analogues which might prove to be equal or more effective then the originally introduced tetracycline families beginning in 1948. Representative of such developments include U.S. Pat. Nos. 3,957,980; 3,674,859; 2,980,584; 2,990,331; 3,062,717; 3,557,280; 4,018,889; 4,024,272; 4,126,680; 3,454,697; and 3,165,531. It will be understood that these issued patents are merely representative of the range of diversity of investigations seeking tetracycline and tetracycline analogue compositions which are pharmacologically active.

Historically, soon after their initial development and introduction, the tetracyclines, regardless of specific formulation or chemical structure, were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic—as for example pneumococci and Salmonella. The rise of tetracycline-resistant organisms has resulted in a general decline in use of tetracyclines and tetracycline analogue compositions as antibiotics of choice.

SUMMARY OF THE INVENTION

The present invention relates to novel chemistries which allow for the production of substituted tetracycline compounds including substituted tetracycline compounds which exhibit significant antibacterial activity. The methods disclosed herein utilize reactive tetracycline-based precursor compounds, reactive organic substituent precursors and transition metals or transition metal catalysts under conditions such that a tetracycline compound substituted with the desired organic substituent is formed. In one embodiment of the invention, a substituted tetracycline compound may be prepared by combining a reactive tetracycline-based precursor compound such as an arene tetracycline diazonium salt, and a reactive organic substituent precursor, e.g., alkenes, substituted alkenes, vinyl monomers, aromatics and heteroaromatics, in the presence of a transition metal catalyst, such as palladium chloride, under conditions such that a tetracycline compound substituted with the organic substituent is formed. In another embodiment, a substituted tetracycline compound may be prepared by contacting a reactive tetracycline chemical complex comprising a reactive tetracycline-based precursor compound and a transition metal or transition metal catalyst forming a reactive chemical intermediate with a reactive organic substituent precursor under conditions such that a tetracycline compound substituted with the organic substituent is formed.

The invention relates in another embodiment to reactive tetracycline chemical complexes comprising a reactive tetracycline-based precursor compound and a transition metal catalyst forming a chemical intermediate, which can advantageously be used in the methods of the invention.

In yet another embodiment substituted tetracycline analogs are disclosed, wherein the substituent (denoted herein as "Z") at the desired position, e.g., 7, 9, 13, is connected with a —C—C— linkage, and wherein the substituent comprises an aromatic or heteroaromatic moiety. The substituent may also comprise a —C═C— bond adjacent to the —C—C— linkage, e.g.,

(Z)

wherein $R_2$ and $R_3$ are each independently hydrogen, alkyl, alkenyl, alkynyl, cycloalkyl, aryl, alkylcarbonyl, arylcarbonyl, alkoxycarbonyl, aryloxycarbonyl, amino, hydroxy, cyano, alkoxy, aryloxy, carboxyl, alkoxycarbonyl, aryloxycarbonyl; or $R_2$ and $R_3$, taken together, form a substituted or unsubstituted carbocyclic or heterocyclic ring having 5 to 15 atoms in the ring.

The methods and chemical intermediates disclosed herein allow for novel substituted tetracycline-type compounds and therapeutic methods and pharmaceutical compositions that comprise such compounds.

The method of the invention includes providing Z substituents, above, on the basic tetracycline ring structure through a process involving forming a reactive intermediate (comprising a tetracycline arenediazonium salt in a preferred embodiment) at the desired position and adding a reactive compound, e.g., a π-bond containing compound in the presence of a transition metal catalyst to that position. The reactive intermediate may be formed in situ. In an advantageous embodiment such substituents are provided on the D ring of the basic tetracycline ring structure, e.g., positions 7 and/or 9. In another advantageous embodiment, such substitutions may be made at position 13. Such synthetic schemes are heretofore new in this art and advantageously allow for direct substitution of different and/or heretofore complex substituent groups at desired positions.

Compounds of the invention are active against susceptible microorganisms, including tetracycline-sensitive bacteria as well as tetracycline-resistant bacteria. Particularly preferred compounds of the invention exhibit 24-hr minimum inhibitory concentration (MIC) values of about 10 μg/mL or less, more preferably about 1 μg/mL or less, against tetracycline-resistant *E. coli*, *S. aureus* and *E. faecalis* strains such as *E. coli* pHCM1, *S. aureus* RN4250 and *E. faecalis* pMV158. Preferred compounds of the invention also include those that exhibit such MIC values against tetracycline-sensitive *E. coli*, *S. aureus* and *E. faecalis* strains such as *E. coli* D31m4, *S. aureus* RN450 and *E. faecalis* ATCC9790.

The invention provides methods of treatment against susceptible microorganisms such as bacteria, fungi, rickettsia, parasites and the like, and diseases associated with such microorganisms. These therapeutic methods in general comprise administration of a therapeutically effective amount of one or more compounds of the invention to a living subject that is suffering from or susceptible to infection by a susceptible microorganism such as bacteria, fungi, rickettsia and the like. Suitable subjects for treatment include animals, particularly a mammal such as human, or plants.

Pharmaceutical compositions comprising one or more compounds of the invention and a suitable carrier are also provided.

DETAILED DESCRIPTION OF THE INVENTION

The present invention will be more fully illustrated by reference to the definitions set forth below.

"Tetracycline" or "tetracycline-type" is intended to include tetracycline and other tetracycline family members such as oxytetracycline; chlortetracycline; demeclocycline; doxycycline; chelocardin; minocycline; rolitetracycline; lymecycline; sancycline; methacycline; apicycline; clomocycline; guamecycline; meglucycline; mepylcycline; penimepicycline; pipacycline; etamocycline; penimocycline, etc. as well as other tetracycline compounds having the characteristic naphthacene A-B-C-D ring structure noted in the Background Of The Invention. Additionally, numbered tetracycline ring positions as referred to herein are the same as designated in the above structural formula.

"Reactive tetracycline-based precursor compound" or "RT-based precursor compound" includes tetracyclines which have a reactive position on the tetracycline ring structure, e.g., at 7, 9 or 13, such that substitution of the reactive tetracycline-based precursor compound may be accomplished as disclosed herein to form a substituted tetracycline compound. Examples of RT-based precursor compounds include derivatives from art-recognized tetracycline compound families. Without limitation, such tetracycline compound families include minocycline, doxycycline and sancycline compounds.

"Minocycline-based precursor compound" is intended to include compounds having the core structure of minocycline, which differs from the core structure of tetracycline by the presence of a dimethylamino group at position 7, and the absence of methyl and hydroxyl groups at position 6, and the absence of a hydroxyl group at position 5. The core structure of minocycline-based precursor compounds is shown below for the purposes of illustration:

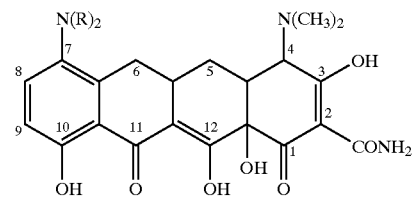

It should be understood that minocycline-based precursor compounds can be substituted, unsubstituted or derivatized, e.g., at positions other than positions 5 and 6. For example, other positions in the core structure, e.g., position 8, can be substituted or unsubstituted and others can be substituted or derivatized, such as the 2-position amido group. Suitable substituents include moieties such as hydrogen, alkyl, alkenyl, alkynyl, cycloalkyl, aryl, alkylcarbonyl, arylcarbonyl, alkoxycarbonyl, aryloxycarbonyl, amino, hydroxy, cyano, alkoxy, aryloxy, carboxyl, carboxamido, carboxy ester, alkoxycarbonyl, aryloxycarbonyl, carbocyclic or heterocyclic groups, and combinations thereof. Other substituent groups will be recognized by those of skill in the art. Further, R in the above formula can represent a group other than methyl, e.g., lower alkyl such as ethyl, propyl, etc. Reactive minocycline-based precursor compounds include, without limitation, 9-diazonium minocycline-based compounds, 9-iodo minocycline-based compounds, 9-bromo minocycline-based compounds, and 9-chloro minocycline-based compounds.

"Doxycycline-based precursor compound" is intended to include compounds having the core structure of doxycycline, which differs from the core structure of tetracycline by the substitution of a hydrogen for a hydroxyl at position 6, and the substitution of a hydroxyl for a hydrogen at position 5. The core structure of doxycycline-based precursor compounds is shown below for the purposes of illustration:

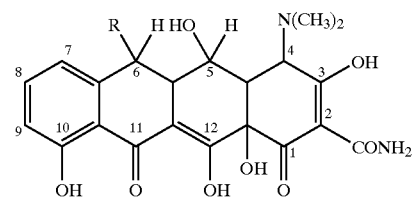

It should be understood that doxycycline-based precursor compounds can be substituted, unsubstituted or derivatized, e.g., at positions 7, 8 and/or 9. For example, other positions in the core structure, e.g., position 8, can be substituted or unsubstituted and others can be substituted or derivatized, such as the 5-position hydroxyl group or the 2-position amido group. Suitable substituents include moieties such as hydrogen, alkyl, alkenyl, alkynyl, cycloalkyl, aryl, alkylcarbonyl, arylcarbonyl, alkoxycarbonyl, aryloxycarbonyl, amino, hydroxy, cyano, alkoxy, aryloxy, carboxyl, carboxamido, carboxy ester, alkoxycarbonyl, aryloxycarbonyl, carbocyclic or heterocyclic groups, and combinations thereof. Other substituent groups will be recognized by those of skill in the art. Further, R in the above formula can represent a group other than methyl, e.g., lower alkyl such as ethyl, propyl, etc. Reactive doxycycline-based precursor compounds include, without limitation, 7- and/or 9-diazonium doxycycline compounds, 7- and/or 9-iodo doxycycline compounds, 7- and/or 9-bromo doxycycline compounds, and 7- and/or 9-chloro doxycycline compounds.

"Sancycline-based precursor compound" is intended to include compounds having the core structure of sancycline, which differs from the core structure of tetracycline by the substitution of a hydrogen for a methyl group and hydrogen for a hydroxyl at position at position 6. The core structure of sancycline-based precursor compounds is shown below for the purposes of illustration:

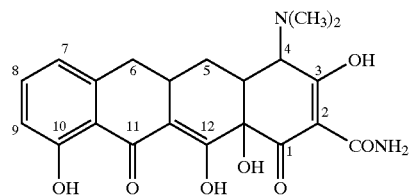

It should be understood that sancycline-based precursor compounds can be substituted, unsubstituted or derivatized, e.g., at positions 7, 8 and/or 9. For example, other positions in the core structure, e.g., position 8, can be substituted or unsubstituted and others can be substituted or derivatized, such as the 2-position amido group. Suitable substituents include moieties such as hydrogen, alkyl, alkenyl, alkynyl, cycloalkyl, aryl, alkylcarbonyl, arylcarbonyl, alkoxycarbonyl, aryloxycarbonyl, amino, hydroxy, cyano, alkoxy, aryloxy, carboxyl, carboxamido, carboxy ester, alkoxycarbonyl, aryloxycarbonyl, carbocyclic or heterocyclic groups, and combinations thereof. Other substituent groups will be recognized by those of skill in the art. Reactive sancycline-based precursor compounds include, without limitation, 7- and/or 9-diazonium sancycline compounds, 7- and/or 9-iodo sancycline compounds, 7- and/or 9-bromo sancycline compounds, and 7- and/or 9-chloro sancycline compounds.

In a preferred embodiment, the reactive tetracycline-based precursor compound is an arene tetracycline diazonium salt, and alternately iodo derivatized tetracycline compounds, or tetracycline compounds that possess a double bond and are reactive with boronic acid derivatives, e.g., at position 13. In one embodiment, the reactive tetracycline-based precursor compound and a transition metal catalyst form a reactive chemical intermediate useful in making novel tetracyclines, through techniques known in the art (see, for example, Hegedus, *Transition Metals in the Synthesis of Complex Organic Molecules*, University Science Books, Mill Valley, Calif., 1994, incorporated herein by reference). The reactive chemical intermediate are preferably formed in situ with the reactive organic substituent precursor.

"Transition metal catalyst" is an art-recognized term which includes transition metals and catalysts comprising a transition metal, e.g., including elements 21 through 29, 39 through 47, 57 through 79, and 89 on. Exemplary transition metal catalysts include $CuCl_2$, copper (I) triflate, copper thiophene chloride, palladium (II) chloride, organopalladium catalysts such as palladium acetate, $Pd(PPh_3)_4$, $Pd(AsPh_3)_4$, $PdCl_2(PhCN)_2$, $PdCl_2(Ph_3P)_2$, $Pd_2(dba)_3$—$CHCl_3$ ("dba"=dibenzylacetone); and combinations thereof. Other transition metal catalysts include those containing metals such as rhodium (e.g. rhodium (II) acetate and $Rh_6(CO)_{16}$), iron, iridium, chromium, zirconium, and nickel. A skilled artisan will be able to select the appropriate transition metal catalyst to perform the desired reaction, based on the existing literature (see, for example, Lipshutz, B. H. *Org. React.* 1992, 41:135, incorporated herein by reference.)

"Reactive organic substituent precursor" includes organic substituents having a reactive group that allows for addition to the reactive tetracycline-based precursor compound as disclosed herein. Preferably the reactive organic substituent precursor comprises at least one reactive group. In an embodiment, the reactive organic substituent precursor may include π-bonded species such as methylene compounds, aryl boronic acids, active aromatic rings and unsubstituted and substituted olefins and alkynes, nitrites, acetylenes, substituted acetylenes, arylethylenes, styrenes, conjugated dienes, isoprenes, vinyl ethers, α,β-unsaturated aldehydes and ketones, aryl vinyl and arylisoprenyl ketones, iodoalkenes and iodoarenes, quinones, α,β-unsaturated acids and their derivatives.

"Reactive organic substituent precursors" also include compounds (which may be formed in situ) which react with the reactive intermediate to form a desired tetracycline analog. For example, the reactive intermediate can be transmetallated to form a wide variety analogs through reactions with other organometal complexes such as tributyltin compounds and lithium diorganocuprates (see for example, Kalanin, *Synthesis*, 1992, 413; Sawamuru, *Chem. Rev.* 1992, 92:857; Negeishi, *Acct. Chem. Res.*, 1982, 15:340, incorporated herein by reference). Other precursors include those suitable for transition metal catalyzed reactions include compounds with bonds which are reactive with the transition metal containing intermediates. Such precursors include, for example, compounds with halogen groups, hydroxyl groups, triflate groups, thiol groups, amino groups. Intramolecular reactions are also included wherein the reactive organic substituent precursor is bonded or associated with the reactive chemical intermediate (see Hegedus, supra).

Compounds of the invention include 7-substituted tetracycline analogs, 9-substituted tetracycline analogs, and 13-substituted tetracycline analogs. These compounds may be illustrated by the general formula

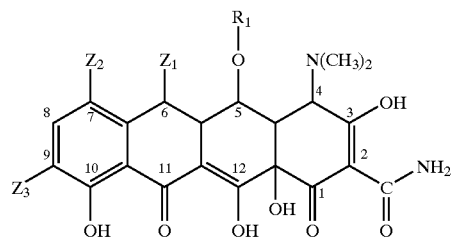

wherein $Z_1$, $Z_2$, and $Z_3$ are individually H or

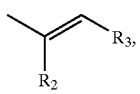

wherein $R_2$ and $R_3$ are each independently hydrogen, alkyl, alkenyl, alkynyl, cycloalkyl, aryl, alkylcarbonyl, arylcarbonyl, alkoxycarbonyl, aryloxycarbonyl, amino, hydroxy, cyano, alkoxy, aryloxy, carboxyl, alkoxycarbonyl, aryloxycarbonyl; or $R_2$ and $R_3$, taken together, form a substituted or unsubstituted carbocyclic or heterocyclic ring having 5 to 15 atoms in the ring; and $R_1$ is H or OH.

In another embodiment $R_2$ is hydrogen, and $R_3$ is

where $R_4$ is hydrogen, cyano, or a $C_1$–$C_5$ alkoxy group.

In another embodiment $R_1$ and $R_2$, taken together, form a substituted or unsubstituted carbocyclic or heterocyclic ring having 5 to 15 atoms in the ring; the ring may be a conjugated or unconjugated aromatic ring system, preferably $C_5$ to $C_8$.

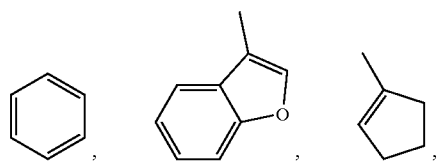

Suitable substituents for Z include

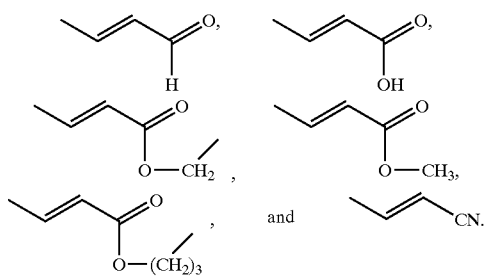

The invention also provides in another aspect a method for preparing substituted tetracycline compounds, desirably 7, 9 or 13-substituted compounds, and, in another aspect, tetracycline compounds prepared by this method. The compounds can be prepared as generally depicted in the Schemes set forth hereinbelow. In the discussions of the Schemes, the various substituent groups are the same as defined above; "R" includes $R_2$ and $R_3$. Also, for purposes of exemplification only, doxycycline is depicted as the "base" tetracycline compound, although it will be understood that a wide variety of tetracycline compounds can be employed in the same manner. For example, the base tetracycline compound substituted at the 7-, 9- and/or 13-positions suitably may be oxytetracycline; chlortetracycline; demeclocycline; doxycycline; chelocardin; minocycline; rolitetracycline; lymecycline; sancycline; methacycline; apicycline; clomocycline; guamecycline; meglucycline; mepylcycline; penimepicycline; pipacycline; etamocycline; penimocycline, semi-synthetic intermediates thereof, and the like.

Tetracycline compounds of the present invention may readily be prepared by the methods outlined in accordance with the following schemes. Scheme I refers to the preparation of tetracycline compounds which may be prepared from a starting compound of formula 1, a clinically useful tetracycline antibiotic named doxycycline. It has been found that 6-(substituted)-5-hydroxy-6-deoxytetracyclines (1, $R_2$=$CH_3$, doxycycline) or their mineral acid salts can be dissolved in concentrated acids, e.g., $H_2SO_4$ as an appropriate solvent, and reacted with nitrating reagents such as sodium or potassium nitrate to produce 7 and 9-nitro tetracycline derivatives (2, 3). These compounds are separated by a variety of techniques, with the preferred method being preparative HPLC on $C_{18}$-reverse phase silica gel with a binary gradient system comprising either phosphate-buffered ethylene diamine tetraacetic acid, sodium salt (EDTA) with a methanol gradient or a gradient of acetonitrile over 0.1% trifluoroacetic acid. These isolated compounds are readily reduced to the amine functional group using typical reducing reagents such as hydrogen with transition metal catalysts, platinum oxide, palladium on carbon, or similar to produce the 7-$NH_2$ and 9-$NH_2$ tetracyclines (4, 5) in good yield. Alternatively, 7-$NH_2$ tetracyclines (doxycycline) can be prepared (such as detailed in U.S. Pat. No. 3,483,251, incorporated herein by reference) via a reductive alkylation of 7-(N,N dicarboxybenzyloxyhydrazino)tetracyclines.

Compounds possessing the anilino functional groups can undergo a diazotization reaction with nitrous acid (HONO) or organic agents such as butyl nitrite readily forming the diazonium salts, (such as the hydrochloride or tetrafluoroborate salts) (6, 7) in nearly quantitative yield. This reactive tetracycline-based precursor compound (6, 7) as a suitable diazonium salt form, can now chemically complex with organopalladium catalysts and species that results in carbon-carbon bond formation between the tetracycline reactant intermediate and the reactive organic substituent precursor of choice. Transition metal catalysts such as $CuCl_2$ (the Meerwin reaction) as well as palladium catalysts such as palladium chloride, palladium acetate or other catalysts mentioned above, with palladium acetate being preferred, are used to produce the 7 and 9 substituted position derivatives of tetracyclines. The reactions are typically run in polar solvents such as DMSO, water, and alcohols with trace mineral acids (HCl, 0.1%) to react with substituted or unsubstituted aromatic or heteroaromatic, alkyl, alkenyl, or alkynyl substructures producing the desired substituted compounds. Non-polar solvents may also be used in which to run the reactions.

It is known that transition metal halides, such as palladium and copper halides, react with arenediazonium salts to form complexes capable of further reactions. Transition metal halides as catalysts facilitate carbon-carbon bond formation via a radical oxidation-reduction addition of carbon substructures (double bonds and other structures possessing π-bonds) to the electron deficient nitrogen diazonium reactive group. For example, palladium catalyzed carbon-carbon bond formation occurs readily when a suitable alkene in the reacting system forms reactive coordination complexes. This is followed by insertion into carbon sigma bonds to give a ternary complex. Catalysts such as palladium are cycled and regenerated via, for example, a β-hydride elimination, thereby forming a carbon-carbon covalent bond. Using these conditions, molecular substructures possessing a π-bond system, such as alkenes or acrylic acid esters or any one of the many other compounds possessing a double bond, are readily arylated with reactive tetracycline-based precursor compounds, e.g., tetracycline arenediazonium salts. Other transition metal catalyzed reactions such as transmetallation and insertion reactions, e.g., of carbon monoxide) are also contemplated (see, Hegedus, supra for examples of transition metal catalyzed reactions).

Homogeneous catalysis of carbon-carbon bond formation is possible using palladium complexes and suitable reactive species. Tetracyclines, e.g., doxycycline or minocycline, are used to generate the reactive diazonium functional group within the D ring while the reactive addend is available from structurally diverse chemical families.

Therefore, reactive tetracycline-based precursor compounds such as tetracycline arenediazonium salts, i.e., having reactive functional groups at, e.g., positions 7 and 9 of the tetracycline molecule similarly can be reacted with alkenes, substituted alkenes, vinyl monomers, aromatic and heteroaromatic reactive groups (unsubstituted or substituted) in the presence of the appropriate transition metal catalyst to produce 7-(substituted) and 9-(substituted) tetracyclines (8, 9, Scheme I) in good yield. 7-position substituted tetracycline 9-diazonium salts, for example (Scheme II), produced by the reaction sequence of minocycline (10) nitration to the 9-$NO_2$ derivative (11), followed by catalytic reduction to the 9-$NH_2$ derivative (12) followed by diazotisation (13), may also be reacted with double bond compounds such as olefins and reactive products and reagents producing minocycline derivatives of formula (II) (14, Scheme II).

In an embodiment, reaction products of formulas I and II may be further derivatized and reacted with reagents as depicted in Schemes II–VII, thus acting as intermediates for making other compounds not readily obtained otherwise. 9-alkenyl substituted doxycyclines (8, 9) of formula I may undergo hydrogenation of the 9-alkenyl group with platinum or palladium catalysts on carbon under low pressure hydrogen to form the 9-alkyl derivatives of doxycycline (15, 16, Scheme III). Similarly, 9-alkenyl derivatives of minocycline (14) may also be reduced to the alkyl derivatives using catalytic hydrogenation methods as shown in Scheme IV (17).

7 or 9 derivatives of doxycycline of formula I (Schemes I and III) may also react with arboxylic acids while dissolved in strong acids such as anhydrous hydrogen fluoride or ethanesulphonic acid or trifluoromethanesulfonic acid to produce the 5-ester derivatives of 7 and 9 substituted doxycyclines (18, 19, Scheme V).

7 or 9 derivatives of doxycycline of formula I (Schemes I, III and V) may also form Mannich base derivatives by the reaction of the 7 or 9 derivatives with formaldehyde and an appropriate base (pyrrolidine) to produce Mannich base addition products (20, 21, Scheme VI).

9 derivatives of minocycline of formula II (14, Scheme II) may also form Mannich base derivatives by the reaction of the 7 or 9 derivative with formaldehyde and an appropriate base (pyrrolidine) to produce the Mannich base addition products (22, Scheme VII).

Tetracycline diazonium reactive functional groups generated in Scheme I may also be reacted with carbon monoxide in alcohols in the presence of transition metal catalysts such as palladium acetate to produce 7 and 9-carboxylic acid derivatives (23, 24) in good yield which readily esterified to produce 9 position tetracycline esters (25, 26, Scheme VII).

Minocycline diazonium reactive functional groups generated in Schemes II may also be reacted with carbon monoxide in alcohols in the presence of transition metal catalysts such as palladium acetate to produce the 9-carboxylic acid derivative (2) in good yield which is readily esterified to produce 9 position minocycline carboxylic acid esters (28, Scheme IX).

Other reactions are possible with 7 and 9 aminotetracyclines via a diazonium functional group. Tetracycline arene diazonium salts also react with active methylene compounds such as esters of acetoacetate, and derivatives thereof, active aromatic rings and unsubstituted and substituted olefins, acetylenes, substituted acetylenes, arylethylenes, styrenes, conjugated dienes, isoprenes, vinyl ethers, α,β-unsaturated aldehydes and ketones, aryl vinyl and arylisoprenyl ketones, quinones, α,β-unsaturated acids and their derivatives. All of the multiple bond compounds are readily coupled to arenediazonium salts, as well as nucleophiles.

Position 7 and the 7 and 9 reactive tetracycline-based precursor compounds (halogenated derivatives of tetracyclines as shown in Scheme X) also produce 7 and 9 derivatives of tetracyclines. Aromatic substitution reactions by iodination, bromination or chlorination to produce the 7 and 9 halogen derivatives of doxycycline (29, 30) or sancycline (31, 32) in good yield by reactions described, e.g., by Hlavka, J. J., et al., J. Am. Chem. Soc., 84, 1961, 1426–1430. Position 7 and 9 halogenated derivatives of the tetracyclines may be further coupled with iodoalkenes or iodoarenes in N-methylpyrrolidinone with transition metal catalysts such as copper thiophene chloride or others to produce the position 7 or 9 derivatives of doxycycline (33, 34) or position 7 or 9 derivatives of doxycycline (35, 36) in good yield.

Position 13-derivatives of tetracyclines may be prepared via the reaction of phenylboronic acids with the exocyclic double bond of methacycline (37) (Scheme XI) in alcohols such as methanol, in the presence of palladium chloride or other transition metal catalysts to produce the 13-phenyl derivatives of methacycline in good yield (38).

The following synthetic schemes are illustrative of the present invention:

Scheme I 7-(substituted)-6-methyl-6-deoxy 5-hydroxy tetracyclines and 9-(substituted)-6-methyl-6-deoxy 5-hydroxy tetracyclines Scheme II 9-(substituted) minocyclines Scheme III 7-(alkyl substituted)-6-methyl-6-deoxy 5-hydroxy tetracyclines and 9-(alkyl substituted)-6-methyl-6-deoxy 5-hydroxy tetracyclines Scheme IV 9-(alkyl substituted) minocyclines Scheme V 7-(alkyl or aryl substituted)-6-methyl-6-deoxy 5-acyloxy tetracyclines and 9-(alkyl or aryl substituted)-6-methyl-6-deoxy 5-acyloxy tetracyclines Scheme VI 7-(alkyl or aryl substituted)-6-methyl-6-deoxy 5-hydoxy tetracyclines and 9-(alkyl or aryl substituted)-6-methyl-6-deoxy 5-hydroxy 2-(carboxamido substituted) tetracyclines Scheme VII 9-(alkyl substituted)-2-(carboxamido substituted) minocyclines Scheme VIII 7-(carboxy or carboxy ester)-6-methyl-6-deoxy 5-hydoxy tetracyclines and 9-(carboxy or carboxy ester)-6-methyl-6-deoxy 5-hydroxy 2-(carboxamido substituted) tetracyclines Scheme IX 9-(carboxy or carboxy ester) minocyclines Scheme X 7-(alkenyl or aryl)-6-methyl-6-deoxy 5-hydoxy tetracyclines and 9-(alkenyl or aryl)-6-methyl-6-deoxy 5-hydroxy tetracyclines, X 9-(alkenyl or aryl)-6-demethyl-6-deoxytetracyclines and 9-(alkenyl or aryl)-6-demethyl-6-deoxytetracyclines Scheme XI 13-(substituted)-6-methylene-5-hydroxy-6-deoxytetracyclines
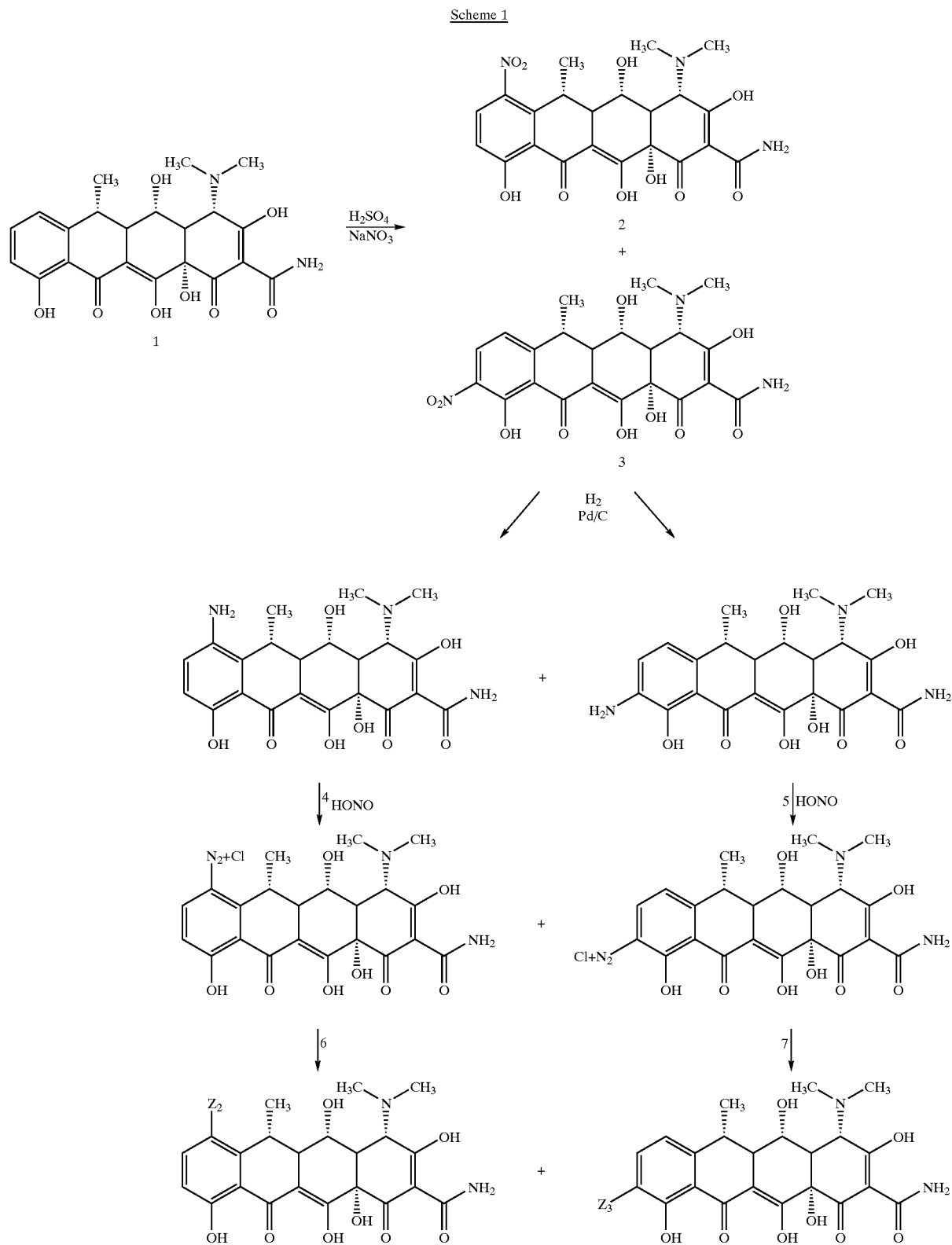

Scheme II
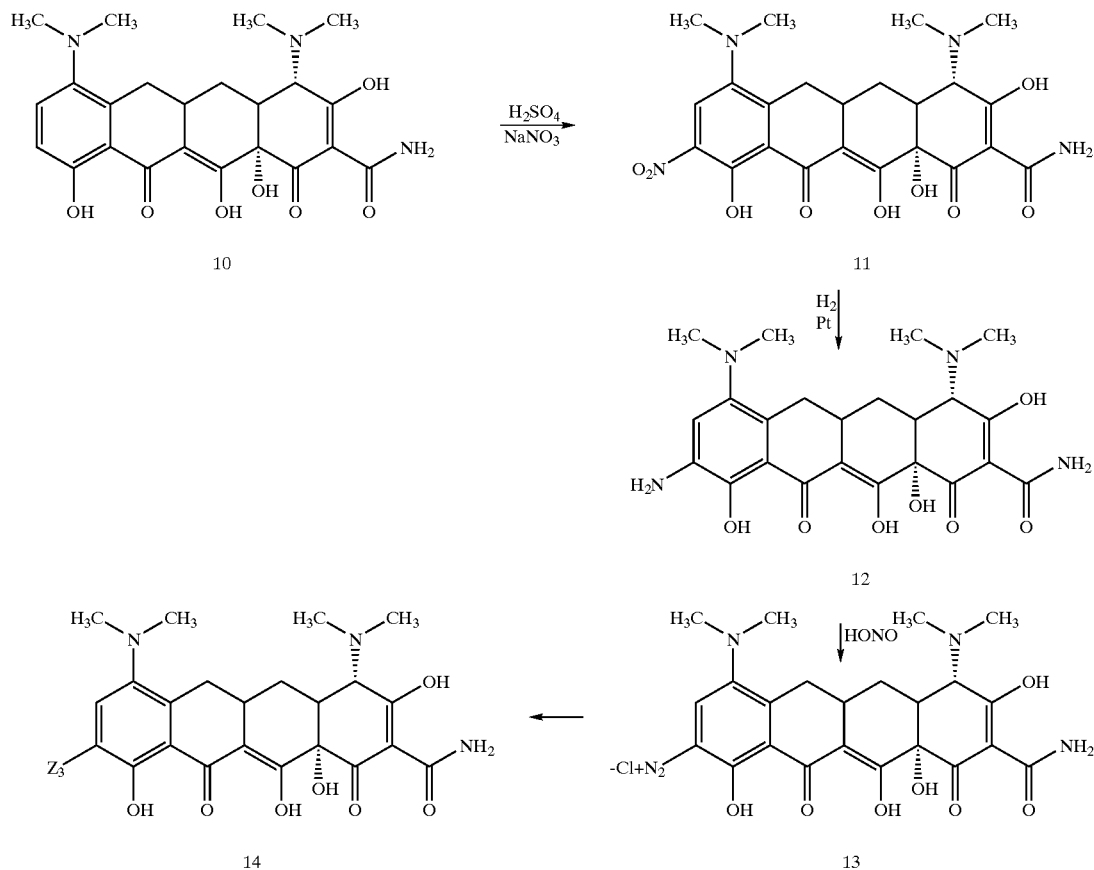
Scheme III
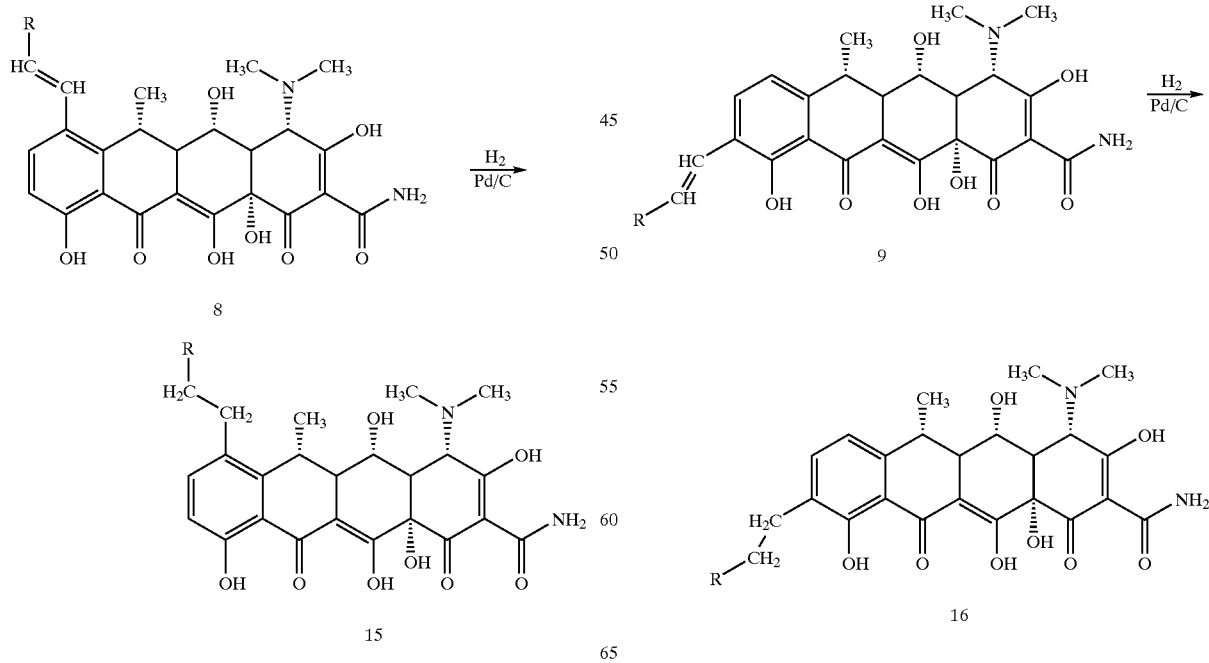

Scheme IV
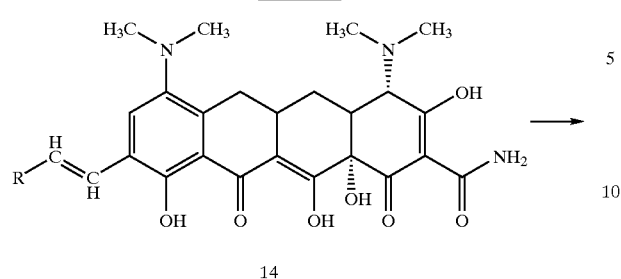
14
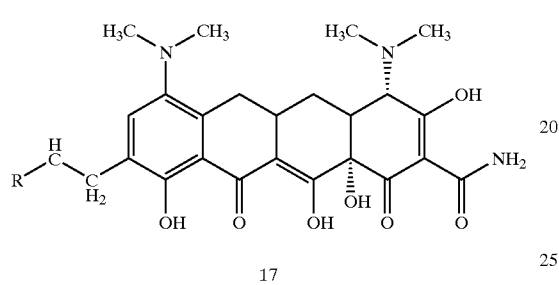
17
Scheme V
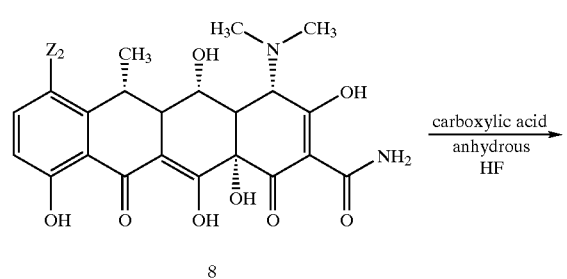
8
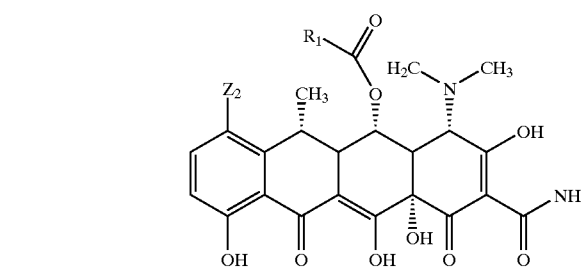
18
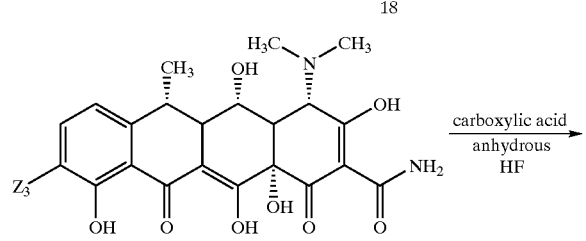
9
-continued
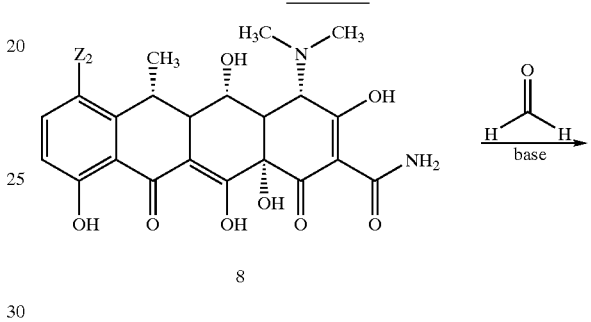
19
Scheme VI
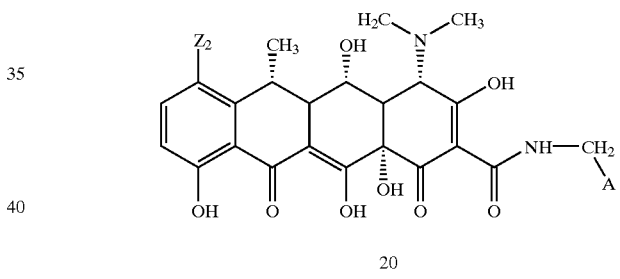
8
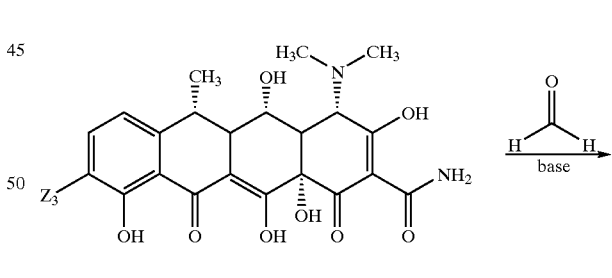
9
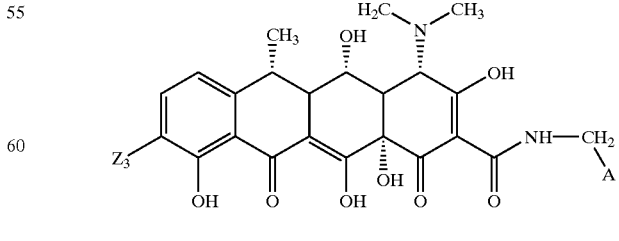
21

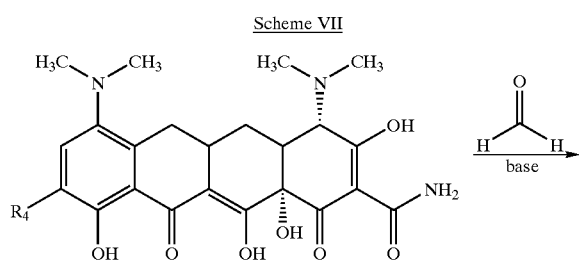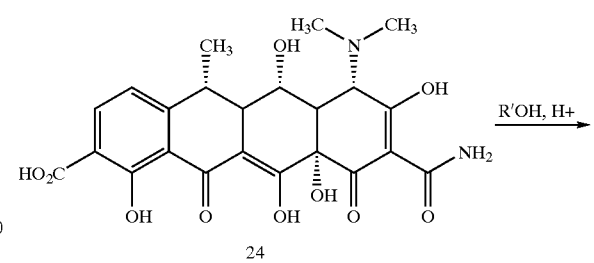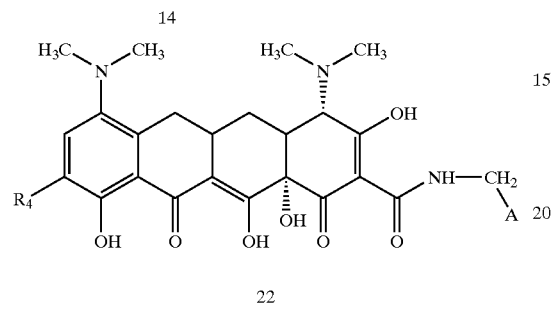

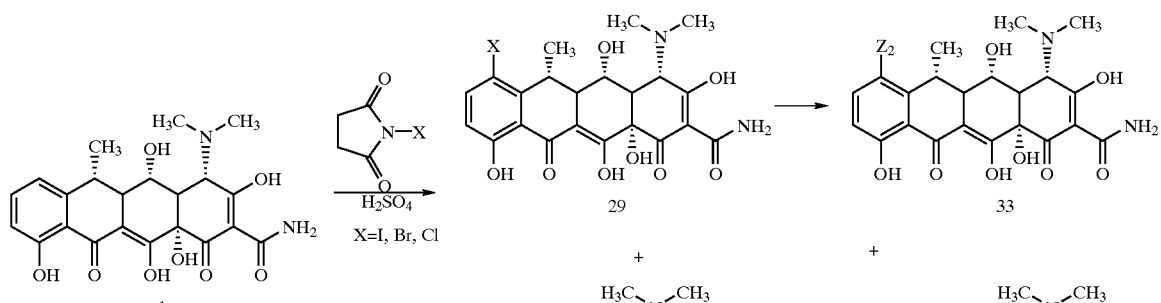
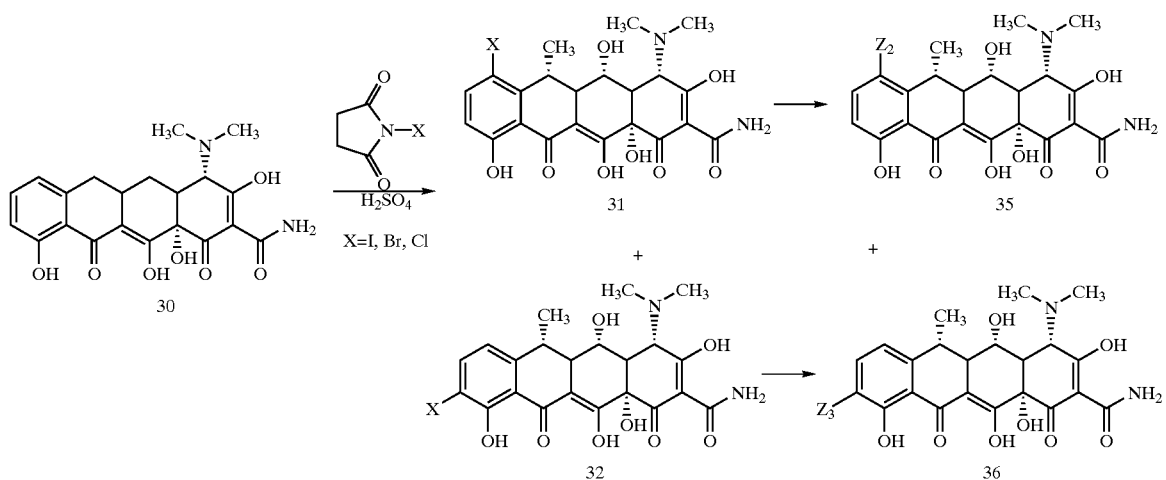
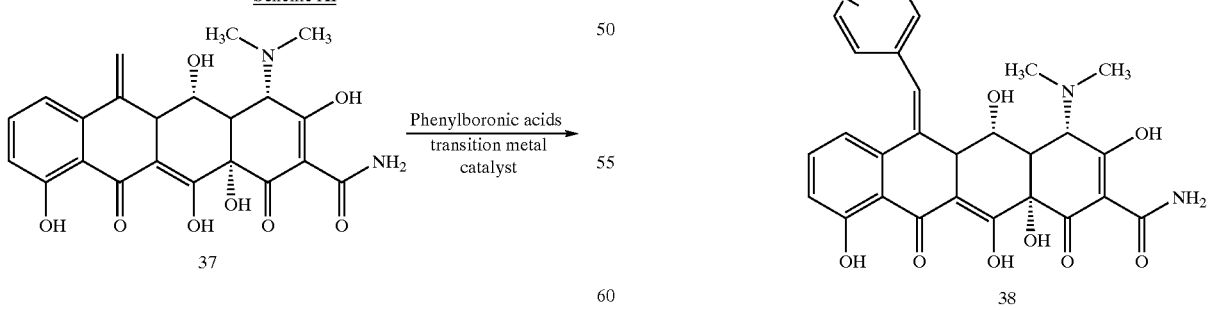
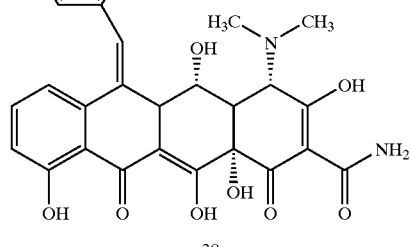

Compounds of the invention are active against susceptible microorganisms such as bacteria, fungi, rickettsia, parasites and the like, and diseases associated with such microorganisms, including tetracycline-sensitive bacteria as well as tetracycline-resistant bacteria. Particularly preferred compounds of the invention exhibit 24-hr minimum inhibitory concentration (MIC) values of about 10 μg/mL or less, more preferably about 1 μg/mL or less, against tetracycline-resistant *E. coli, S. aureus* and *E. faecalis* strains such as *E. coli* pHCM1, *S. aureus* RN4250 and *E. faecalis* pMV158. Preferred compounds of the invention also include those that exhibit such MIC values against tetracycline-sensitive *E. coli, S. aureus* and *E. faecalis* strains such as *E. coli* D31m4, *S. aureus* RN450 and *E. faecalis* ATCC9790.

As discussed above, the invention provides methods of treatment against microorganism infections and associated diseases, which methods in general will comprise administration of a therapeutically effective amount of one or more compounds of the invention to a subject, which may be an animal or plant, and typically is a mammal, preferably a primate such as a human.

In therapeutic methods of the invention, one or more compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

At least many of the compounds of the invention suitably may be administered to a subject in a protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. Also, where an appropriate acidic group is present on a compound of the invention, a pharmaceutically acceptable salt of an organic or inorganic base can be employed such as an ammonium salt, or salt of an organic amine, or a salt of an alkali metal or alkaline earth metal such as a potassium, calcium or sodium salt.

Therapeutic compounds can be administered to a subject in accordance with the invention by any of a variety of routes. Topical (including transdermal, buccal or sublingual), and parenteral (including intraperitoneal, subcutaneous, intravenous, intradermal or intramuscular injection) are generally preferred.

For parenteral application, particularly suitable are solutions, preferably oily or aqueous solutions as well as suspensions, emulsions, or implants, including suppositories. Therapeutic compounds will be formulated in sterile form in multiple or single dose formats such as being dispersed in a fluid carrier such as sterile physiological saline or 5% saline dextrose solutions commonly used with injectables.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

In addition to treatment of humans, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of 0.01 to 100 milligrams per kilogram of bodyweight of recipient per day, preferably in the range of 0.1 to 50 milligrams per kilogram bodyweight of recipient per day, more preferably in the range of 1 to 20 milligrams per kilogram bodyweight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Biological Activity

Method for in vitro Evaluation

Various compounds made in accordance with the invention were evaluated for antibacterial activity in vitro as follows. The minimum inhibitory concentration, the lowest concentration of drug that inhibits bacterial growth at 18 hrs at their appropriate temperature, is determined by the broth dilution method using L-broth or Mueller-Hinton broth. The Mueller-Hinton broth was cation-adjusted accordingly and all bacteriological methods were performed as was described by Waitz, J. A., National Commission for Clinical Laboratory Standards Document M7-A2, vol.10, no. 8, pp.13–20, $2^{nd}$ edition, Villanova, Pa. (1990). The organisms tested represent gram-positive and gram-negative bacterial species that are susceptible to tetracyclines or are resistant to tetracyclines due to the ability to efflux tetracyclines or which confer resistance by ribosomal protection mechanisms. The clinical strains used are either susceptible to tetracyclines or are resistant to them by either drug efflux or ribosomal protection.

TABLE I

LEGEND FOR COMPOUNDS

| Compound | Name |
| --- | --- |
| Doxycycline | [4S-(4a,12aα)]-4-(dimethylamino)-1,4,4a,5,5a,6,11,12a-octahydro-3,5,10,12,12a-pentahydroxy-6-methyl-1,11-dioxo-2-naphthacenecarboxamide |
| Minocycline | [4S-(4a,12aα)]-4,7-Bis(dimethylamino)-1,4,4a,5,5a,6,11,12a-octahydro-3,10,12,12a-tetrahydroxy-1,11-dioxo-2-naphthacenecarboxamide |
| A | [4S-(4a,12aα)]-9-(nitro)-4-(dimethylamino)-1,4,4a,5,5a,6,11,12a-octahydro-3,5,10,12,12a-pentahydroxy-6-methyl-1,11-dioxo-2-naphthacenecarboxamide (9-nitro-6-deoxy-5-hydroxy tetracycline) |
| B | [4S-(4a,12aα)]-9-(amino)-4-(dimethylamino)-1,4,4a,5,5a,6,11,12a-octahydro-3,5,10,12,12a-pentahydroxy-6-methyl-1,11-dioxo-2-naphthacenecarboxamide (9-amino-6-deoxy-5-hydroxy tetracycline) |
| C | [4S-(4a,12aα)]-9-(diazonium)-4-(dimethylamino)-1,4,4a,5,5a,6,11,12a-octahydro-3,5,10,12,12a-pentahydroxy-6-methyl-1,11-dioxo-2-naphthacenecarboxamide (9-diazonium-6-deoxy-5-hydroxy tetracycline) |
| D | [4S-(4a,12aα)]-9-[3'-(E)-propenoic acid]-4-(dimethylamino)-1,4,4a,5,5a,6,11,12a-octahydro-3,5,10,12,12a-pentahydroxy-6-methyl-1,11-dioxo-2-naphthacenecarboxamide (9-[3'-(E)-ethylpropenoic acid]-6-deoxy-5-hydroxy tetracycline) |
| E | [4S-(4a,12aα)]-9-[3'-(E)-butylpropenoate]-4-(dimethylamino)-1,4,4a,5,5a,6,11,12a-octahydro-3,5,10,12,12a-pentahydroxy-6-methyl-1,11-dioxo-2-naphthacenecarboxamide (9-[3'-(E)-butylpropenoate]-6-deoxy-5-hydroxy tetracycline) |
| F | [4S-(4a,12aα)]-9-[3'-(E)-butylpropenoate]-4,7-Bis(dimethylamino)-1,4,4a,5,5a,6,11,12a-octahydro-3,10,12,12a-tetrahydroxy-1,11-dioxo-2-naphthacenecarboxamide 9-[3'-(E)-butylpropenoate]minocycline |
| G | [4S-(4a,12aα)]-7-[4'-Cl-phenyl)]-4-(dimethylamino)-1,4,4a,5,5a,6,11,12a-octahydro-3,10,12,12a-tetrahydroxy-1,11-dioxo-2-naphthacenecarboxamide 7-(4'-Cl-phenyl)sancycline |
| H | [4S-(4a,12aα)]-7-phenyl-9-phenyl-4-(dimethylamino)-1,4,4a,5,5a,6,11,12a-octahydro-3,10,12,12a-tetrahydroxy-1,11-dioxo-2-naphthacenecarboxamide 7,9-diphenyl sancycline |
| I | [4S-(4a,12aα)]-13-(4'-methylphenyl)-4-(dimethylamino)-1,4,4a,5,5a,6,11,12a-octahydro-3,5,10,12,12a-pentahydroxy-6-methylene-1,11-dioxo-2-naphthacenecarboxamide 13-(4'-methylphenyl)-6-deoxy-6-methylene-5-hydroxy tetracycline |
| J | [4S-(4a,12aα)]-13-(3'-carboxyphenyl)-4-(dimethylamino)-1,4,4a,5,5a,6,11,12a-octahydro-3,5,10,12,12a-pentahydroxy-6-methylene-1,11-dioxo-2-naphthacenecarboxamide 13-(3'-carboxyphenyl)-6-deoxy-6-methylene-5-hydroxy tetracycline |
| K | [4S-(4a,12aα)]-13-(4'-ethoxyphenyl)-4-(dimethylamino)-1,4,4a,5,5a,6,11,12a-octahydro-3,5,10,12,12a-pentahydroxy-6-methylene-1,11-dioxo-2-naphthacenecarboxamide 13-(4'-ethoxyphenyl)-6-deoxy-6-methylene-5-hydroxy tetracycline |

TABLE II

Antibacterial Activity of Transition Metal Catalyzed Derivatives of Tetracyclines

| | Doxy | D | E | F | G | H | I | J | K |
| --- | --- | --- | --- | --- | --- | --- | --- | --- | --- |
| E. coli ML308-225 Tc$^s$ | 0.78 | 25 | 6.25 | >50 | >50 | >50 | >50 | >50 | 12.5 |
| E. coli D1-299 Tc$^r$ | 25 | >50 | >50 | >50 | >50 | >50 | >50 | >50 | >50 |
| E. coli D1-209 Tc$^r$ | 50 | >50 | >50 | >50 | >50 | >50 | >50 | >50 | >50 |
| E. coli D31m4 Tc$^s$ | 1.56 | >50 | 3.12 | 3.12 | 0.78 | 1.56 | 6.25 | >50 | 12.5 |
| E. coli D 31m4 pHCM1 Tc$^r$ | 25 | >50 | 6.25 | 6.25 | 0.78 | — | 25 | >50 | >50 |

TABLE II-continued

Antibacterial Activity of Transition Metal Catalyzed Derivatives of Tetracyclines

|  | Doxy | D | E | F | G | H | I | J | K |
|---|---|---|---|---|---|---|---|---|---|
| S. aureus RN450 Tc$^s$ | <0.098 | 3.12 | 0.78 | 1.56 | ≦0.098 | 1.56 | ≦0.098 | 0.39 | 0.195 |
| S. warnerii Tc$^r$ | 50 | >50 | 6.25 | 3.12 | ≦0.098 | 0.78 | 12.5 | >50 | 12.5 |
| ATCC 12715 S. aureus RN4250 Tc$^r$ | 25 | >50 | 6.25 | 3.12 | ≦0.098 | 0.78 | 12.5 | >50 | 6.25 |
| S. aureus MRSA5 Tc$^r$ | 6.25 | >50 | 0.39 | 3.12 | 0.195 | 0.78 | 6.25 | >50 | 6.25 |
| E. hirae ATCC9790 Tc$^s$ | 0.195 | 3.12 | 3.12 | 3.12 | ≦0.098 | 0.78 | 0.39 | 3.12 | 0.39 |
| E. hirae 9790 with pMV158 Tc$^r$ | 6.25 | 12.5 | 6.25 | 3.12 | ≦0.098 | 0.39 | 3.12 | >50 | 6.25 |
| E. hirae 9790 with pAM211 Tc$^r$ | 6.25 | >50 | 6.25 | 3.12 | ≦0.098 | 1.56 | 12.5 | >50 | 3.12 |

Tc$^s$ = tetracycline susceptible
Tc$^r$ = tetracycline resistant

Experimental

Compounds of the invention may be prepared as presented in schemes I through IX, above, and/or as described below.

In scheme I, doxycycline is dissolved in cold concentrated sulfuric acid and an equivalent of potassium nitrate is added. The reaction temperature was maintained in the range 0 to 5° C. for a period of 1 to 3 hrs, producing 7 and 9-nitro-6-substituted-5-hydroxy tetracyclines of formula IV. These intermnediates, with suitable chemically reactive functionality, can be reacted with a broad range of reducing agents such as PtO$_2$ or hydrogen and palladium or platinum catalysts producing compounds of general formula IV. The diazonium salts of the 7 and 9 amino derivatives are produced by the action of nitrites (sodium nitrite, butyl nitrite or equivalent) and the intermediate used without further purification.

EXAMPLE 1

[4S-(4α,12aα)]-9-(Nitro)-4-(dimethylamino)-1,4,4a,5,5a,6,11,12a-octahydro-3,5,10,12,12a-pentahydroxy-6-methyl-1,11-dioxo-2-naphthacenecarboxamide To an ice cold solution of 1.0 g of doxycycline hydrochloride in 10 mL of concentrated sulfuric acid was added 0.231 g of potassium nitrate. The reaction was stirred for 1 hr under ambient atmosphere. The mixture was then poured over 150 g of ice and the resulting solid was extracted with n-butanol and dried to afford 0.9 g of the desired product as a yellow-green solid.

MS(FAB): m/z 490 (M+H). $^1$H NMR (CD$_3$OD): δ 7.50 (d, 1H, J=8.07 Hz, H-8); 6.86 (d, 1H, J=8.07 Hz, H-7); 4.44 (bs, 1H, H-4); 3.62 (dd, 1H, J=11.42 ; 8.35 Hz, H-5); 2.95 (bs, 6H, NMe$_2$); 2.81 (d, 1H, J=11.45 Hz, H-4a); 2.71 (dq, 1H, J=12.41; 6.5 Hz, H-6); 2.53 (dd, 1H, J=12.23; 8.20 Hz, H-5a); 1.51 (d, 3H, J=6.78 Hz, CH$_3$).

EXAMPLE 2

[4S-(4α,12aα)]-9-(Amino)-4-(dimethylamino)-1,4,4a,5,5a,6,11,12a-octahydro-3,5,10,12,12a-pentahydroxy-6-methyl-1,11-dioxo-2-naphthacenecarboxamide Into a 200 mL hydrogenation bottle is added 1.0 g of product from example 1, 40 mL of methanol, 1 mL of concentrated HCl, and 100 mg of 10% palladium on carbon. Using a hydrogenation apparatus, the mixture is subjected to 30 psi of hydrogen for 3 hrs. The catalyst is filtered off and the filtrate is dried to afford 0.9 g of the dihydrochloride as a yellow solid.

MS(FAB): m/z 460 (M+H).

$^1$H NMR (CD$_3$OD): d 7.54 (d, 1H, J=8.08 Hz, H-8); 6.88 (d, 1H, J=8.08 Hz, H-7); 5.16 (dd, J=10.44; 7.94 Hz, H-5); 4.44 (bs, 1H, H-4); 3.74 (d, 1H, J=2.07 Hz, H-4); 3.04 (bs, 6H, NMe$_2$); 2.90 (dd, 1H, J=7.94; 2.07 Hz, H-4a); 2.72 (dq, 1H, J=12.31; 6.56 Hz, H-6); 2.61 (dd, 1H, J=12.31; 10.44 Hz, H-5a); 2.54 (q, 2H, J=7.48 Hz, CH$_2$—C); 1.44 (bs, 9H, CMe$_3$); 1.29 (d, 3H, J=6.56 Hz, CH$_3$); 1.20 (t, 3H, J=7.48 Hz, C—CH$_3$).

EXAMPLE 3

[4S-(4α,12aα)]-9-(Diazonium)-4-(dimethylamino)-1,4,4a,5,5a,6,11,12a-octahydro-3,5,10,12,12a-pentahydroxy-6-methyl-1,11-dioxo-2-naphthacenecarboxamide A 10 mL round bottom flask was charged with 100 mg of product from example 2 and dissolved in 4 mL of 0.1 N methanolic hydrochloric acid. The solution was cooled to 0° C. and 35 μl of butyl nitrite was added with stirring. After 1 hr, the bright red reaction mixture was added dropwise to 100 mL of cold anhydrous diethyl ether. The product was collected by filtration, washed with ether, and dried in a vacuum dessicator to give 73 mg of the diazonium salt as an orange solid.

MS(FAB): m/z 472 (M+H).

$^1$H NMR (CD$_3$OD): d 7.55 (d, 1H, J=8.08 Hz, H-8); 6.86 (d, 1H, J=8.08 Hz, H-7); 5.13 (dd, J=10.44; 7.94 Hz, H-5); 4.41 (bs, 1H, H-4); 3.72 (d, 1H, J=2.07 Hz, H-4); 3.04 (bs, 6H, NCH$_3$); 2.90 (dd, 1H, J=7.94; 2.07 Hz, H-4a); 2.70 (dq, 1H, J=12.31; 6.56 Hz, H-6); 2.61 (dd, 1H J=12.31; 10.44 Hz, H-5a); 2.2 (m, 6H, J=7.48 Hz, Acetyl); 1.44 (bs, 9H, C(CH$_3$)$_3$); 1.29 (d, 3H, J=6.56 Hz, CH$_3$); 1.20 (t, 3H, J=7.48 Hz, C—CH$_3$).

General procedure for olefination. To a solution of 0.1 g of 9-diazonium compound in (wet or dry) methanol is added 0.05 equivalents of palladium acetate. The reaction mixture is stirred for 5 minutes at room temperature, and 2 equivalents of the desired olefin is added. Stirring is continued for 18 hrs under ambient atmosphere or followed by HPLC. The stirring may also be continued under $N_2$ atmosphere. Upon completion, the catalyst is filtered off and the filtrate dried to give the crude product. The purified product is isolated by preparative reverse-phase HPLC using methanol and phosphate buffer gradient.

EXAMPLE 4

[4S-(4α,12aα)]-9-[3'-(E)-Propenoic Acid]-4-(dimethylamino)-1,4,4a,5,5a,6,11,12a-octahydro-3,5,10,12,12a-pentahydroxy-6-methyl-1,11-dioxo-2-naphthacenecarboxamide MS(FAB): m/z 515 (M+H).

EXAMPLE 5

[4S-(4α,12aα)]-9-[1'-(E)-(2'-Phenyl)ethenyl]4-(dimethylamino)-1,4,4a,5,5a,6,11,12a-octahydro-3,5,10,12,12a-pentahydroxy-6-methyl-1,11-dioxo-2-naphthacenecarboxamide MS(FAB): m/z 547 (M+H).

EXAMPLE 6

[4S-(4α,12aα)]-7-[3'-(E)-Butylpropenoate]4-(dimethylamino)-1,4,4a,5,5a,6,11,12,12a-octahydro-3,5,10,12,12a-pentahydroxy-6-methyl-1,11-dioxo-2-naphthacenecarboxamide General procedure for arylation. To a solution of 9-diazonium compound in methanol is added 0.10 equivalents of palladium acetate. The mixture is stirred at room temperature for 5 minutes, and 2 equivalents of aryl boronic acid is added. After 6 hrs, the catalyst is filtered off and the filtrate is dried down. The crude product is purified by preparative reverse-phase HPLC using a methanol phosphate buffer gradient.

General procedure for carboxylation. To a three neck round bottom flask equipped with two rubber septa, a vacuum source, and a stir bar, is added 100 mg of diazonium compound, 6.0 mg of palladium acetate, and 10 mL of anhydrous dimethylformamide. The reaction vessel is evacuated, and CO is passed through the mixture for 1 hr via a syringe. The mixture is stirred for an additional 2 hr, then the solvent removed in vacuo to yield the crude product. The title compound was isolated by preparative $C_{18}$ reverse-phase HPLC by using a binary solvent gradient.

EXAMPLE 7

[4S-(4α,12aα)]-9-(Carboxy)-4-(dimethylamino)-1,4,4a,5,5a,6,11,12a-octahydro-3,5,10,12,12a-pentahydroxy-6-methyl-1,11-dioxo-2-naphthacenecarboxamide MS(FAB): m/z 489 (M+H).

General procedure for hydrogenation. The compound is prepared by dissolving 0.100 g of Example 4 into 10 mL of methanol, adding 0.1% concentrated HCl and 10 mg of 10% palladium on carbon. The mixture is hydrogenated in at 40 psi in a Parr apparatus for 6 hrs at room temperature and monitored by HPLC. The resulting crude product is chromatographed on $C_{18}$ reverse-phase via semi-preparative binary solvent methods to give the desired product. General procedure for 7 position olefination. To a solution of 0.1 g of 7-diazonium compound, generated in similar methods as described in Examples 1 and 2, in wet methanol is added 0.05 equivalents of palladium acetate. The reaction mixture is stirred for 5 minutes at room temperature, and 2 equivalents of the desired olefin are added. Stirring is continued for 18 hrs under ambient atmosphere and followed by HPLC. Upon completion, the catalyst is filtered through Celite and the filtrate dried to give the crude product. The purified product is isolated by preparative reverse-phase HPLC using methanol and phosphate buffer gradient.

EXAMPLE 8

9-phenyl Minocyctine
[4S-(4α,12aα)]-9-(phenyl)-4,7-Bis(dimethylamino)-1,4,4a,5,5a,6,11,12a-octahydro-3,5,10,12,12a-tetrahydroxy-6-methyl-1,11-dioxo-2-naphthacenecarboxamide The compound was prepared using 0.100 g of 9-amino minocycline and reagents and conditions similar to those found in Example 5. The reaction was stirred overnight under a nitrogen atmosphere and the solvent removed in vacuo to produce 0.063 g of the crude product. Chromatography using $C_{18}$ reverse-phase preparative methods and binary solvent systems followed by extraction of the product into butanol and evaporation of the product in vacuo, furnished 0.027 g of the desired product as a yellow solid.

MS(FAB): m/z 571 (M+H).

EXAMPLE 9

7-iododoxycycline 30.0 mL of concentrated sulfuric acid was added to 1.00 g of doxycycline hydrochloride hemihydrate with stirring and the solution cooled to 0° C. 0.973 g of N-iodosuccinimide was added portionwise to the solution over one hr and the reaction monitored by HPLC and TLC to ensure completion. The solution was poured into 250 mL of ice water, extracted three times with butanol, and the solvent removed under reduced pressure. The crude residue was purified by preparative HPLC to provide 1.13 g (89%) of the title compound as dark yellow crystals.

MS (FAB): m/z 587 (M+H).

$^1$H NMR (Methanol d-4, 300 MHz) δ 7.94 (d, J=8.19 Hz, 1H), 6.78 (d, J=8.18 Hz, 1H), 4.13 (s, 1H), 3.53 (m, 3H), 2.85 (s, 7H), 2.66 (m, 4H), 2.41 (s, 1H), 1.49 (d, J=6.52 Hz, 3H), 0.95 (t, J=7.27 Hz, 2H).

EXAMPLES 10 AND 11

7-iodosancycline and 7,9-diiodosancyline 30.0 mL of concentrated sulfuric acid was added to 1.00 g of sancycline hydrochloride hemihydrate with stirring and the solution cooled to 0° C. 1.09 g of N-iodosuccinimide was added portionwise to the solution over one hr and the reaction mixture monitored by HPLC and TLC. The reaction mixture was poured into 250 mL of ice water, extracted three times with n-butanol, and the solvent removed under reduced pressure. The crude residue was purified by preparative HPLC yielding 787 mg (61%) of 7-iodosancycline and 291 mg (22%) of 7,9-diiodosancycline as yellow and dark yellow crystals respectively.

MS (FAB): m/z 587 (M+H) 7-iodosancycline $^1$H NMR (Methanol d-4, 300 MHz) δ 7.89 (d, J=8.86 Hz, 1H), 6.67 (d, 8.87 Hz, 1H), 3.56 (s, 1H), 3.03 (s, 2H), 2.84 (s, 6H), 2.46 (m, 2H), 1.63 (m, 4H) 0.95 (m, 2H).

MS (FAB): m/z 667 (M+H) 7,9-dilodosancycline $^1$H NMR (Methanol d-4, 300 MHz) δ 8.35 (s, 1H), 3.78 (s, 1H), 3.33 (s, 2H), 2.88 (s, 7H), 2.41 (m, 2H), 1.41 (m, 5H).

EXAMPLE 12

General Coupling Procedure 7-4'-Cl-phenyl sancycline 100 mg of 7-iodosancycline or 7-iodo doxycycline (0.18 mM) and 4 mg of Pd(OAc)$_2$ is added to an argon degassed solution of methanol followed by 200 µl of 2 M Na$_2$CO$_3$. The resultant solution was stirred for 10 minutes at room temperature. 4'-Cl-phenyl boronic acid (58 mg, 0.37 mM) was dissolved in 1 mL methanol, added to the iodotetracycline and the reaction flask degassed with argon 3 times. The reaction was stirred for 15 minutes at room temperature, then heated to reflux for 18 hrs. The solution was cooled, filtered and the solvent removed under reduced pressure. The crude product was purified by C18-reverse phase chromatography to yield 23 mg of product as dark yellow crystals.

MS (FAB): m/z (M+H) 525.1852.

$^1$H NMR (Methanol d$_4$, 300 MHz) δ 7.35–7.44 (m, 4H), 7.21–7.24 (d, 1H), 6.85–6.88 (d, 1H), 3.55 (s, 1H), 2.88 (s, 6H), 2.47 (m, 2H) 1.52 (m, 2H)

EXAMPLE 13

7,9-diphenyl Sancycline

MS (FAB) m/z (M+H) 567.2545.

$^1$H NMR (Methanol d4, 300 MHz) δ 7.22–7.85 (m, 11H), 4.02 (m, 1H), 3.53 (s, 1H), 2.86 (br s, 6H), 2.41 (m, 2H), 1.52 (m, 2H)

EXAMPLE 14

7-(4-fluorophenyl)sancycline

MS (FAB): m/z 509 (M+H).

$^1$H NMR (Methanol d-4, 300 MHz) δ 7.41 (d, J=8.61 Hz, 1H), 7.30 (td, J=6.87, 2.16 Hz, 2H), 7.16 (td, J=6.84, 2.11 Hz, 2H), 6.89 (d, J=8.59 Hz, 1H) 3.56 (s, 2H), 2.91 (s, 7H), 1.52 (m, 4H), 0.95 (m, 2H).

EXAMPLE 15

7-(4-nitrophenyl)sancycline

MS (FAB): m/z 536 (M+H).

$^1$H NMR (Methanol d-4, 300 MHz) δ 8.28 (d, J=8.50, 2H), 7.52 (d, J=8.52, 2H), 7.42 (d, J=8.64, 1H), 6.93 (d, J=8.65, 1H), 3.51 (s, 2H), 6.73 (s, 7H), 1.50 (m, 5H), 0.92 (m, 2H).

EXAMPLE 16

7-(2-pyridyl)doxycycline

MS (FAB): m/z 522 (M+H).

$^1$H NMR (Methanol d-4, 300 MHz) δ 8.62 (s, 1H), 7.94 (m, 2H), 7.49 (m, 1H), 7.40 (m, 1H), 6.94 (m, 1H), 4.21 (s, 1H), 3.56 (m, 2H), 2.91 (s, 7H), 2.70 (m, 3H), 1.038 (s, 3H), 0.92 (m, 2H).

EXAMPLE 17

7-ethylenylsancycline

MS (FAB): m/z 471 (M+H).

$^1$H NMR. (Methanol d-4, 300 MHz) δ 7.65 (d, J=8.79 Hz, 1H), 6.80 (d, J=8.76 Hz, 1H), 5.56 (d, J=18.42 Hz, 1H), 5.25 (d, J=12.15 Hz, 1H), 3.84 (s, 1H), 3.19 (m, 2H), 2.98 (s, 6H), 2.82 (m, 1H), 2.32 (m, 2H), 0.92 (m, 1H).

EQUIVALENTS

Those skilled in the art will recognize, or be able to ascertain using no more than routine experimentation, numerous equivalents to the specific procedures described herein. Such equivalents are considered to be within the scope of this invention and are covered by the following claims. The contents of all references, issued patents, and published patent applications cited throughout this application are hereby incorporated by reference.

What is claimed is:

1. A 7-substituted tetracycline analog, wherein said substituent at the 7 position is connected with a —C—C— linkage, and wherein said substituent is substituted or unsubstituted phenyl.

2. A 7-substituted tetracycline analog, wherein said analog is 7-4'-Cl-phenyl sancycline.

3. A 7-substituted tetracycline analog, wherein said analog is 7-(4-fluorophenyl)sancycline.

4. A 7-substituted tetracycline analog, wherein said analog is 7-(4-nitrophenyl)sancycline.

5. The 7-substituted tetracycline analog of claim 1, wherein said tetracycline analog is 7-substituted oxytetracycline or demeclocycline.

6. The 7-substituted tetracycline analog of claim 1, wherein said tetracycline analog is 7-substituted doxycycline.

7. The 7-substituted tetracycline analog of claim 1, wherein said tetracycline analog is 7-substituted chelocardin, rolitetracycline, or lymecycline.

8. The 7-substituted tetracycline analog of claim 1, wherein said tetracycline analog is 7-substituted sancycline.

9. The 7-substituted tetracycline analog of claim 1, wherein said tetracycline analog is 7-substituted methacycline.

10. The 7-substituted tetracycline analog of claim 1, wherein said tetracycline analog is 7-substituted apicycline, guamecycline, or meglucycline.

11. The 7-substituted tetracycline analog of claim 1, wherein said tetracycline analog is 7-substituted penimepicycline, pipacycline, or penimocycline.

12. The 7-substituted tetracycline analog of claim 1, wherein said substituent is

13. The 7-substituted tetracycline analog of claim 1, wherein said analog has an MIC value of 10 µg/mL or less against tetracycline-resistant strains of *E. coli, S. aureus* or *E. faecalis*.

14. The 7-substituted tetracycline analog of claim 13, wherein said analog has an MIC value of 1 µg/mL or less against tetracycline-resistant strains of *E. coli, S. aureus* or *E. faecalis*.

15. The 7-substituted tetracycline analog of claim 1, wherein said analog has an MIC value of 10 µl g/m or less against tetracycline sensitive strains of *E. coli, S. aureus* or *E. faecalis*.

16. The 7-substituted tetracycline analog of claim 15, wherein said analog has an MIC value of 1 µg/mL or less against tetracycline sensitive stains of *E. coli, S. aureus* or *E. faecalis*.

17. A pharmaceutical composition, comprising a 7-substituted tetracycline analog of claim 1 and a pharmaceutically acceptable carrier.

18. A pharmaceutical composition comprising a 7-substituted tetracycline analog of claim 2 and a pharmaceutically acceptable carrier.

19. A pharmaceutical composition, comprising a 7-substituted tetracycline analog of claim 3 and a pharmaceutically acceptable carrier.

20. A pharmaceutical composition, comprising a 7-substituted tetracycline analog of claim 4 and a pharmaceutically acceptable carrier.

21. A pharmaceutical composition, comprising a 7-substituted tetracycline analog of claim 12 and a pharmaceutically acceptable carrier.

22. A pharmaceutical composition, comprising a 7-substituted tetracycline analog of claim 13, and a pharmaceutically acceptable carrier.

23. A pharmaceutical composition, comprising a 7-substituted tetracycline analog of claim 14, and a pharmaceutically acceptable carrier.

24. A pharmaceutical composition, comprising a 7-substituted tetracycline analog of claim 15, and a pharmaceutically acceptable carrier.

25. A pharmaceutical composition, comprising a 7-substituted tetracycline analog of claim 16, and a pharmaceutically acceptable carrier.

* * * * *